United States Patent
DeSimone et al.

(10) Patent No.: US 11,969,197 B2
(45) Date of Patent: Apr. 30, 2024

(54) METHODS AND DEVICES FOR ELECTROPORATION FOR TREATMENT OF VENTRICULAR FIBRILLATION

(71) Applicant: Mayo Foundation for Medical Education and Research, Rochester, MN (US)

(72) Inventors: Christopher V. DeSimone, Rochester, MN (US); Samuel J. Asirvatham, Rochester, MN (US); Christopher J. McLeod, Ponte Vedra Beach, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 110 days.

(21) Appl. No.: 16/754,935

(22) PCT Filed: Oct. 15, 2018

(86) PCT No.: PCT/US2018/055869
§ 371 (c)(1),
(2) Date: Apr. 9, 2020

(87) PCT Pub. No.: WO2019/075459
PCT Pub. Date: Apr. 18, 2019

(65) Prior Publication Data
US 2020/0305946 A1 Oct. 1, 2020

Related U.S. Application Data

(60) Provisional application No. 62/572,253, filed on Oct. 13, 2017.

(51) Int. Cl.
*A61B 18/00* (2006.01)
*A61B 18/14* (2006.01)

(52) U.S. Cl.
CPC .......... *A61B 18/00* (2013.01); *A61B 18/1492* (2013.01); *A61B 2018/0022* (2013.01);
(Continued)

(58) Field of Classification Search
CPC ........ A61B 18/1492; A61B 2018/0022; A61B 2018/00577; A61B 2018/00613
See application file for complete search history.

(56) References Cited

U.S. PATENT DOCUMENTS

| 4,166,113 A | 8/1979 | Norton et al. |
| 4,819,751 A | 4/1989 | Shimada et al. |

(Continued)

FOREIGN PATENT DOCUMENTS

| CA | 2158051 | 9/1994 |
| WO | WO 2011/159641 | 12/2011 |

(Continued)

OTHER PUBLICATIONS

Haïssaguerre et al., "Mapping and ablation of idiopathic ventricular fibrillation," Circulation, Aug. 2002, 106(8):962-967.
(Continued)

*Primary Examiner* — Jaymi E Della
*Assistant Examiner* — Abigail M Ziegler
(74) *Attorney, Agent, or Firm* — Fish & Richardson P.C.

(57) ABSTRACT

This document describes methods and devices for treating ventricular fibrillation. For example, this document describes methods of performing electroporation of a ventricle and electroporation catheters. The methods can include inserting a distal end portion of a catheter into a ventricle of a heart of a patient, inflating a balloon coupled to the distal end portion of the catheter, occluding a valve of the heart associated with the ventricle with the balloon, injecting a fluid into the ventricle via an aperture defined by the distal end portion of the catheter, and generating an (Continued)

electrical current via an electrode on the distal end portion of the catheter.

10 Claims, 10 Drawing Sheets

(52) U.S. Cl.
CPC ............... *A61B 2018/00238* (2013.01); *A61B 2018/00285* (2013.01); *A61B 2018/00357* (2013.01); *A61B 2018/00577* (2013.01); *A61B 2018/00613* (2013.01); *A61B 2018/00648* (2013.01); *A61B 2018/00654* (2013.01); *A61B 2018/00708* (2013.01); *A61B 2018/0072* (2013.01); *A61B 2018/00744* (2013.01); *A61B 2018/00839* (2013.01); *A61B 2018/00875* (2013.01)

(56) References Cited

U.S. PATENT DOCUMENTS

| | | | |
|---|---|---|---|
| 5,860,974 | A | 1/1999 | Abele |
| 6,023,638 | A * | 2/2000 | Swanson ............... A61B 5/6855 606/41 |
| 6,086,582 | A | 7/2000 | Altman et al. |
| 7,190,997 | B1 | 3/2007 | Darvish et al. |
| 7,736,346 | B2 | 6/2010 | Miller et al. |
| 8,036,741 | B2 | 10/2011 | Jahns et al. |
| 11,541,241 | B2 | 1/2023 | Asirvatham |
| 2001/0041890 | A1 * | 11/2001 | Hassett ............... A61B 18/1492 606/41 |
| 2002/0151812 | A1 | 10/2002 | Scheiner et al. |
| 2009/0099560 | A1 * | 4/2009 | Rioux ................ A61M 25/1011 606/41 |
| 2011/0144028 | A1 | 6/2011 | Sharma |
| 2012/0143099 | A1 * | 6/2012 | Daniels ............. A61M 25/0029 606/14 |
| 2013/0066315 | A1 | 3/2013 | Subramaniam et al. |
| 2013/0253616 | A1 | 9/2013 | Libbus et al. |
| 2014/0081111 | A1 * | 3/2014 | Tun ......................... A61B 5/287 600/374 |
| 2015/0132409 | A1 | 5/2015 | Stein et al. |
| 2016/0051324 | A1 | 2/2016 | Stewart et al. |
| 2016/0058504 | A1 | 3/2016 | Davies et al. |
| 2016/0113709 | A1 * | 4/2016 | Maor ................ A61B 18/1492 606/41 |
| 2016/0249978 | A1 * | 9/2016 | Lee ....................... A61B 1/3137 600/476 |
| 2016/0270845 | A1 | 9/2016 | Benscoter et al. |
| 2016/0310211 | A1 * | 10/2016 | Long .................. A61B 18/1492 |
| 2017/0035499 | A1 | 2/2017 | Stewart et al. |
| 2017/0042614 | A1 * | 2/2017 | Salahieh ............ A61M 25/1011 |
| 2017/0065339 | A1 | 3/2017 | Mickelsen |
| 2017/0105793 | A1 | 4/2017 | Cao et al. |
| 2017/0189097 | A1 | 7/2017 | Viswanathan et al. |
| 2017/0340888 | A1 | 11/2017 | Callas et al. |
| 2018/0085159 | A1 * | 3/2018 | Sulkin ................ A61B 18/1233 |
| 2018/0214196 | A1 * | 8/2018 | Eum ..................... A61B 18/082 |
| 2019/0105057 | A1 * | 4/2019 | Radl ................ A61B 17/12109 |
| 2020/0205890 | A1 * | 7/2020 | Harlev ............... A61B 18/1492 |
| 2020/0298008 | A1 | 9/2020 | Asirvatham |
| 2023/0149718 | A1 | 5/2023 | Asirvatham |

FOREIGN PATENT DOCUMENTS

| | | |
|---|---|---|
| WO | WO 2014/143898 | 9/2014 |
| WO | WO 2014/195933 | 12/2014 |
| WO | WO 2017/062753 | 4/2017 |
| WO | WO 2017/074920 | 5/2017 |

OTHER PUBLICATIONS

Haïssaguerre et al., "Role of Purkinje conducting system in triggering of idiopathic ventricular fibrillation," Lancet, Feb. 2002, 359(9307):677-678.
International Preliminary Report on Patentability in Application No. PCT/US2018/055869 dated Apr. 14, 2020, 7 pages.
International Search Report & Written Opinion in Application No. PCT/US2018/055869 dated Jan. 2, 2019, 14 pages.
Livia et al., "Electroporative Elimination of Purkinje Fibers Reduces Vulnerability to Ventricular Fibrillation," Presented at Heart Rhythm Society in May 11-12, 2017, 1 page.
Lopera et al., "Identification and ablation of three types of ventricular tachycardia involving the his-purkinje system in patients with heart disease," J. Cardiovasc. Electrophysiol., 2004, 15(1):52-58.
Nogami et al., "Mapping and ablation of idiopathic ventricular fibrillation from the Purkinje system," Heart Rhythm, 2005, 2(6):646-649.
Odening et al., "Electro-Mechanical Remodeling in Transgenig Short QT Syndrome Rabbits," Poster C-PO04-01:S327, Heart Rhythm Society in May 11-12, 2017, 1 page.
Witt et al., "Electroporative Myocardial Ablation Utilizing a Non-contact, Virtual Electrode: Proof of Concept in Ex-vivo and In-vivo Canine Hearts," Presented at Heart Rhythm Society in May 11-12, 2017, 14(5):S327-S417.
U.S. Appl. No. 16/763,712, filed May 13, 2020, Samuel J. Asirvatham, Published.
Boyden et al., "Cardiac Purkinje fibers and arrhythmias; The GK Moe Award Lecture 2015," Hearth Rhythm, May 2016, 13(5):1172-1181.
Damiano Jr. et al., "The effect of chemical ablation of the endocardium on ventricular fibrillation threshold," Circulation, Sep. 1986, 74(3):645-652.
DeSimone et al., "Novel balloon catheter device with pacing, ablating, electroporation, and drug-eluting capabilities for atrial fibrillation treatment—preliminary efficacy and safety studies in a canine model," Transl. Res., Dec. 2014, 164(6):508-514.
Evans Jr. et al., "Predictors of in-hospital mortality after DC catheter ablation of atrioventricular junction. Results of a prospective, international, multicenter study," Circulation, Nov. 1991, 84(5):1924-1937.
Frühling et al., "Single-center nonrandomized clinical trial to assess the safety and efficacy of irreversible electroporation (IRE) ablation of liver tumors in humans: Short to mid-term results," Eur. J. Surg. Oncology, Apr. 2017, 43(4):751-757.
Hou et al., "Determination of ventricular vulnerable period and ventricular fibrillation threshold by use of T-wave shocks in patients undergoing implantation of cardioverter/defibrillators," Circulation, Nov. 1, 1995, 92(9):2558-2564.
Hwang et al., "Upper limit of vulnerability reliably predicts the defibrillation threshold in humans," Circulation, Nov. 1994, 90(5):2308-2314.
Knecht et al., "Long-term follow-up of idiopathic ventricular fibrillation ablation: a multicenter study," J. Am. Coll. Cardiology, Aug. 4, 2009, 54(6):522-528.
Lemery et al., "Low energy direct current ablation in patients with the Wolff-Parkinson-White syndrome: clinical outcome according to accessory pathway location," Pacing Clin. Electrophysiology, Nov. 1991, 14(11 Pt 2):1951-1955.
Minners et al., "Dinitrophenol, cyclosporin A, and trimetazidine modulate preconditioning in the isolated rat heart: support for a mitochondrial role in cardioprotection," Cardiovasc. Research, Jul. 2000, 47(1):68-73.
Neven et al., "Epicardial linear electroporation ablation and lesion size," Heart Rhythm, Aug. 2014, 11(8):1465-1470.
O'Núnáin et al., "Catheter ablation by low energy DC shocks for successful management of atrial flutter," Br. Heart Journal, Jan. 1992, 67(1):67-71.
Santoro et al., "Ventricular fibrillation triggered by PVCs from papillary muscles: clinical features and ablation," J. Cardiovasc. Electrophysiology, Nov. 2014, 25(11):1158-1164.

(56) References Cited

OTHER PUBLICATIONS

Sutter et al., "Safety and Efficacy of Irreversible Electroporation for the Treatment of Hepatocellular Carcinoma Not Amenable to Thermal Ablation Techniques: A Retrospective Single-Center Case Series," Radiology, Sep. 2017, 284(3):877-886.

Swerdlow et al., "Comparative reproducibility of defibrillation threshold and upper limit of vulnerability," Pacing Clin. Electrophysiology, Dec. 1996, 19(12 Pt 1):2103-2111.

Valerio et al., "Nanoknife Electroporation Ablation Trial: A Prospective Development Study Investigating Focal Irreversible Electroporation for Localized Prostate Cancer," J. Urology, Mar. 2017, 197(3 Pt 1):647-654.

Van Driel et al., "Pulmonary vein stenosis after catheter ablation: electroporation versus radiofrequency," Circ. Arrhythm. Electrophysiology, Aug. 2014, 7(4):734-738.

Vogel et al., "Induction Chemotherapy Followed by Resection or Irreversible Electroporation in Locally Advanced Pancreatic Cancer (IMPALA): A Prospective Cohort Study," Ann. Surg. Oncology, Sep. 2017, 24(9):2734-2743.

Witt et al., "Electroporative Myocardial Ablation Utilizing a Non-contact, Virtual Electrode: Proof of Concept in Ex-vivo and In-vivo Canine Hearts," Poster, Presented at Heart Rhythm Society, May 11-12, 2017, 1 page.

Wittkampf et al., "Myocardial lesion depth with circular electroporation ablation," Circ. Arrhythm, Electrophysiology, Jun. 1, 2012, 5(3):581-586.

Yeh et al., "Simplified Method for Concentration of Mitochondrial Membrane Protein Complexes," Electrophoresis, Jun. 2010, 31(12):1934-1936.

Kleinhaus et al., "The effects on canine cardiac Purkinje fibers of Chrysaora quinquecirrha (sea nettle) toxin," Toxicon, Jul. 1973, 11(4):341-349.

Spiro et al., "Use of left ventricular support devices during acute coronary syndrome and percutaneous coronary intervention," Curr. Cardiol. Rep., Dec. 2014, 16(12):544.

Chen et al., "Comparison of the defibrillation threshold and the upper limit of ventricular vulnerability," Circulation, May 1986, 73(5):1022-1028.

Livia et al., "Abstract #: C-PO04-139: Electroporative Elimination of Purkinje Fibers Reduces Vulnerability to Ventricular Fibrillation," Heart Rhythm, May 2017, 14(5):S383, 2 pages.

Livia et al., "Elimination of Purkinje Fibers by Electroporation Reduces Ventricular Fibrillation Vulnerability," J. Am. Heart Assoc., Aug. 2018, 7(15):e009070, 9 pages.

McLeod et al., "Delayed ischemic preconditioning activates nuclear-encoded electron-transfer chain gene expression in parallel with enhanced postanoxic mitochondrial respiratory recovery," Circulation, Aug. 2004, 110:534-539.

\* cited by examiner

METHODS AND DEVICES FOR ELECTROPORATION FOR TREATMENT OF VENTRICULAR FIBRILLATION

CROSS-REFERENCE TO RELATED APPLICATIONS

This application is a National Stage application under 35 U.S.C. §371 of International Application No. PCT/US2018/055869, having an International Filing Date of Oct. 15, 2018, which claims priority to U.S. application Ser. No. 62/572,253, filed on Oct. 13, 2017. The disclosure of the prior application is considered part of the disclosure of this application, and is incorporated in its entirety into this application.

BACKGROUND

1. Technical Field

This document relates to methods and materials for treating ventricular fibrillation. For example, this document relates to methods and devices for electroporation of Purkinje tissue to treat ventricular fibrillation.

2. Background Information

Sudden cardiac death is a leading cause of mortality, the majority of which is due to ventricular fibrillation. Further, ventricular fibrillation is the most common terminal arrhythmia in humans. Occurring either as a primary event or secondary event to concomitant cardiac and non-cardiac diseases and events, prevention of this arrhythmia remains rudimentary. Although defibrillators and anti-arrhythmics provide an element of protection in select cases, sudden cardiac death remains a major worldwide health problem.

Electroporation is a technique that uses high voltage to non-thermally introduce multiple nanopores within the cells' wall, specifically within the lipid bilayer of the cell membranes as a result of the change in electrical field. Depending on the voltage and frequency of pulsations used, these pores can be reversible (i.e., increase the permeability of these cell to chemotherapeutic agents) and or irreversible (i.e., trigger cell death by the process of apoptosis or necrosis). Given the different composition of each cell-type membrane, electroporation can allow for a differential effect on different tissues.

SUMMARY

This document describes methods and materials for treating ventricular fibrillation. For example, this document describes methods and devices for electroporation of Purkinje tissue to treat ventricular fibrillation.

In one aspect, this disclosure is directed to a method of performing electroporation of a ventricle. In some cases, the method can include inserting the distal end portion of a catheter into a ventricle into the heart of a patient, inflating a balloon coupled to the distal end portion of the catheter, occluding a valve of the heart associated with the ventricle with the balloon, injecting a fluid into the ventricle via an aperture defined by the distal end portion of the catheter, and generating an electrical current via an electrode on the distal end portion of the catheter, wherein the electrical field is conducted by the fluid to cause non-thermal electroporation. In some cases, the electrode can be located on the outer surface of a balloon. In some cases, the balloon can include a porous section to allow the fluid to pass through the balloon. In some cases, the method can include removing blood from the ventricle. In some cases, the method can include removal of blood from the ventricle, in order to provide contact between the catheter and the tissue. In some cases, the method can include removal of blood from the ventricle with the catheter serving as a means to re-circulate blood from the ventricle to the aorta as part of the catheter shaft. In some cases, the catheter and the shaft form part of a feedback circuit to provide hemodynamic stability of the patient, for example, in a case of hypotension from heart failure or refractory ventricular arrhythmias. In some cases, the method can include injecting alternating cycles of saline and an osmotic reagent. In some cases, the method can include sensing signals from Purkinje fibers. In some cases, the method can include modifying a parameter of the electrical current or a concentration of the fluid based on the signals. In some cases, a feedback circuit could be used based on the electrical signals from the catheter, impedance from the catheter tip, and/or hemodynamic support via fluid or the patient's own transfused blood.

In another aspect, this disclosure is directed to an electroporation catheter. In some cases, the electroporation catheter can include a distal end portion defining an aperture, an electrode located on the distal end portion, and a balloon coupled to the distal end portion. In some cases, the aperture can allow for injection of a fluid through a lumen defined by the catheter. In some cases, the aperture can be located at a distal end of the catheter and can be in fluid communication with a proximal aperture. In some cases, the proximal aperture can be located in the ascending or descending aorta. In some cases, a proximal aperture and a distal aperture can allow blood, or other fluids, to bypass from the ventricle to the aorta in order to provide hemodynamic support and stability. In some cases, the balloon can be proximal to the electrode and the aperture. In some cases, the balloon can be shaped to occlude a heart valve when inflated. In some cases, the electroporation catheter can include a sensing electrode. In some cases, the sensing electrode can sense signals from Purkinje fibers. In some cases, the electrode can be located on the balloon.

In yet another aspect, this disclosure is directed to an electroporation catheter. In some cases, the electroporation catheter can include a distal end portion defining an aperture, an electrode located on the distal end portion, and a balloon extending along a portion of the distal end portion. In some cases, the aperture can allow for injection of a fluid through a lumen defined by the catheter. In some cases, the balloon can include a porous section that allows for the fluid to pass through the balloon. In some cases, the balloon can surround the electrode. In some cases, the balloon can be shaped to occlude and extend into a heart valve when inflated. In some cases, the electroporation catheter can include a sensing electrode.

Particular embodiments of the subject matter described in this document can be implemented to realize one or more of the following advantages. The methods and devices for electroporation can limit damage to conduction tissue and muscle by selectively targeting tissues for ablation based on differences in tissue response. The systems and methods can provide superficial ablations that are far reaching to accommodate variations in the shape of the ventricle. In some cases, the systems and methods can provide hemodynamic support similar to an Impella or ECMO circuit by using the catheter and shaft as ports for inflow and outflow of blood and/or other fluids. Such a method can enhance catheter stability as well as hemodynamic support during mapping and ablation of tissue. Alternatively, deeper and more specific ablation can also be provided. Treatment can include ventricular fibrillation ablation, ventricular tachycardia ablation, myocardial specific ablation, and/or ganglia ablation. Treatment can also include vessel avoidance and provide modulation of treatment. Further, ablation can be provided within minimal damage to healthy heart tissue. As the Purkinje network is involved in both the triggering and sustainment of ventricular arrhythmias, modifying the Purkinje cell membrane potential via a drug (e.g., through the mechanism of action of the drug, or a delivery of the drug) can provide a means to terminate arrhythmias through slowing electrical conduction or prolonging cell refractoriness.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings and from the claims.

DESCRIPTION OF DRAWINGS

Like reference numbers represent corresponding parts throughout.

DETAILED DESCRIPTION

This document describes methods and materials for treating ventricular fibrillation. For example, this document describes methods and devices for electroporation of Purkinje tissue to treat ventricular fibrillation.

Ventricular fibrillation is the most common terminal arrhythmia in humans. Electroporation is a technique that uses rapid bursts of DC current to non-thermally introduce multiple nanopores with the cells' walls of surrounding tissue. The Purkinje system has been implicated in the genesis of primary ventricular fibrillation, with ablation of focal Purkinje triggers successfully treating the arrhythmia, which can be achieved using electroporation. The methods and devices provided herein can ablate the widespread Purkinje tissue with minimal damage to healthy heart tissue which can be reversible and used for electroporation-mapping, modulation of purkinje signals to evaluate effect, utilized to temporarily break the arrhythmia, or irreversible with complete destruction of purkinje tissue.

Figure 1:
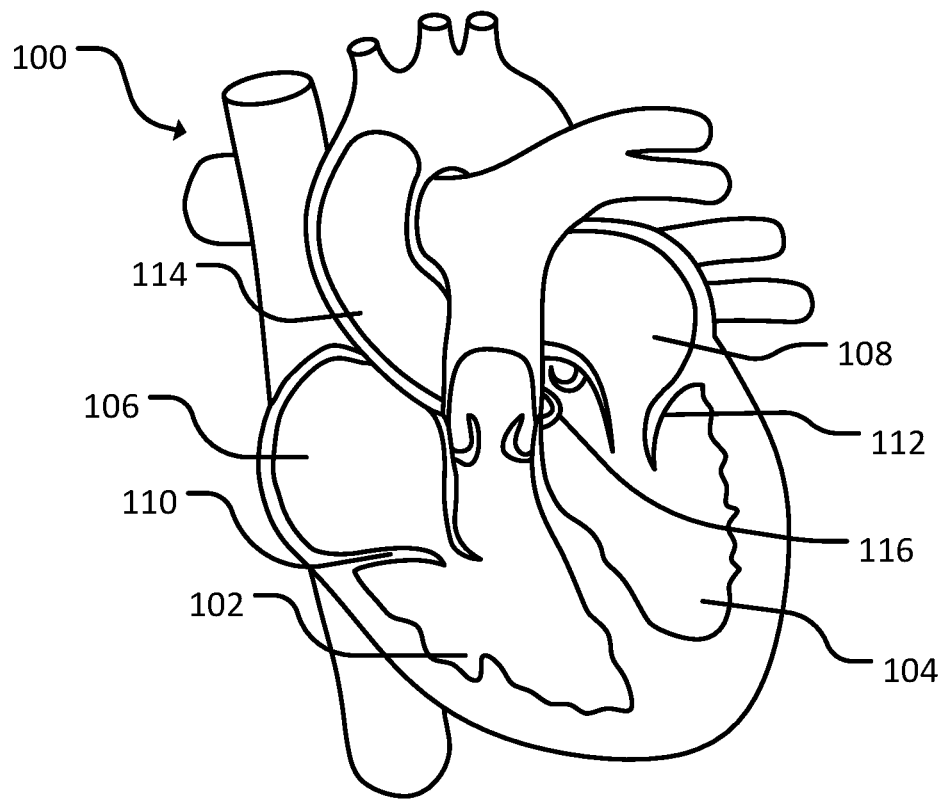
FIG. 1 is a cross-sectional view of a human heart.

Referring to FIG. 1, a heart 100 includes a right ventricle 102, a left ventricle 104, a right atrium 106, and a left atrium 108. A tricuspid valve 110 is located between right atrium 108 and right ventricle 102. A mitral valve 112 is located between left atrium 108 and left ventricle 104. A semilunar valve 116 is located between left ventricle 104 and aorta 116. Right ventricle 102 and/or left ventricle 104 can include Purkinje tissue. Purkinje fibers can be located in the inner ventricular walls of the heart and are specialized conducting fibers that allow the heart's conductive system to create synchronized contractions to maintain a consistent heart rhythm. Purkinje fibers can be superficial in right ventricle 102 and/or left ventricle 104. In some cases, there can be millions of Purkinje fibers. Purkinje fibers can also initiate tachyarrhythmias, such as those that cause ventricular fibrillation.

As described further below, devices and methods for administering electroporation to the right ventricle 102 or the left ventricle 104 are provided herein. Moreover, using the provided devices and methods for administering electroporation, the Purkinje fibers can be targeted. In some cases, using the provided devices and methods, a catheter can be used as part of a system for hemodynamic support during ablation. Using such devices and techniques, treatment of ventricular fibrillation can be achieved.

Figure 2:
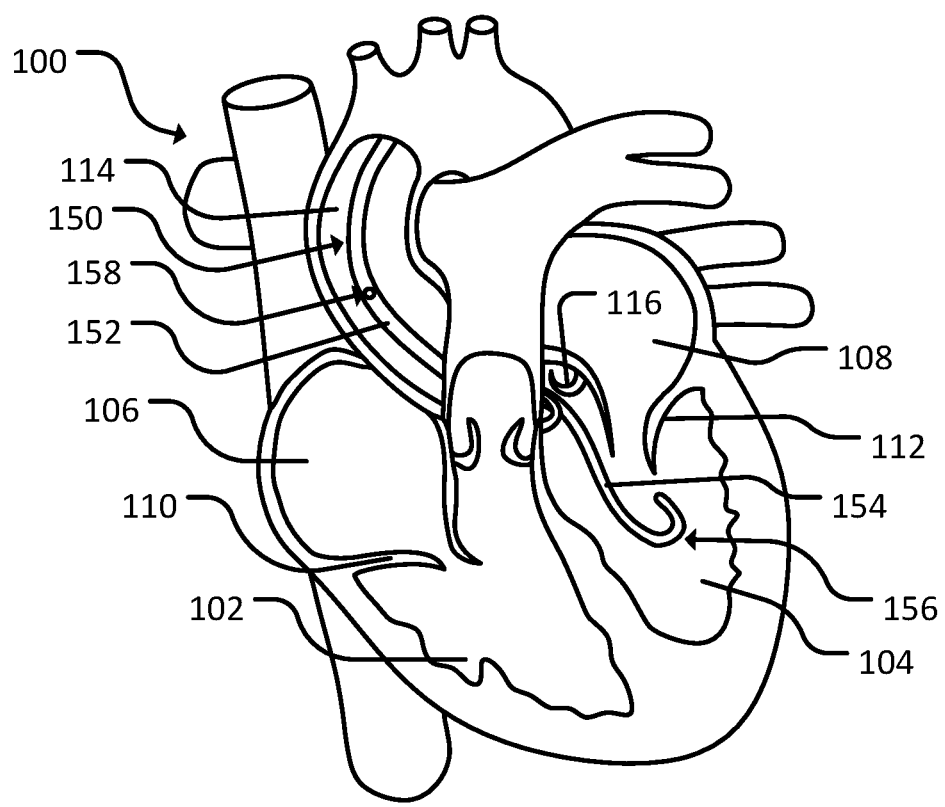
FIG. 2 is a schematic diagram of a first catheter assembly in a heart, in accordance with some embodiments provided herein.
Figure 3:
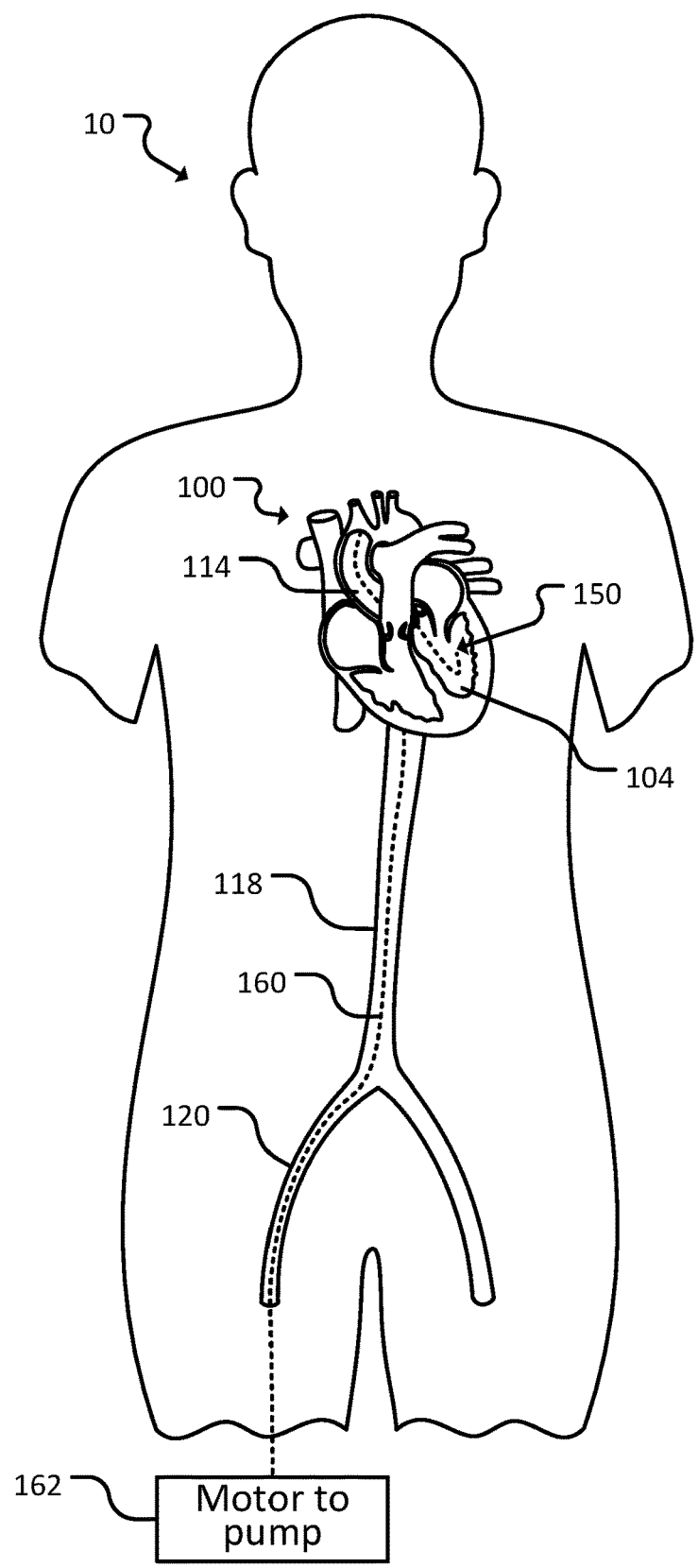
FIG. 3 is a schematic diagram of the first catheter assembly of FIG. 2 in a patient, in accordance with some embodiments provided herein.

Referring to FIGS. 2 and 3, a first catheter assembly 150 can include a proximal portion 152 and a distal portion 154. First catheter assembly 150 can be guided to heart 100 of a patient 10 by entering a femoral artery 120 and passing through the systemic arteries 118 into aorta 114 of heart 100. First catheter assembly 150 can then pass through the semilunar valve 116 into left ventricle 104. In some cases, first catheter assembly 150 can be navigated into left ventricle 104 using a retrograde aortic approach. In some cases, first catheter assembly 150 can be navigated into left ventricle 104 using a transseptal approach.

Proximal portion 152 can reside in the ascending or descending aorta 114, while the distal portion 154 resides in the left ventricle 104. Catheter assembly 150 can include a proximal extension portion 160 that provides communication between proximal portion 152, distal portion 154, and a motor 162. In some cases, motor 162 can provide pumping of first catheter assembly 150.

Proximal portion 152 can include an aperture 158 that can provide inflow and outflow of blood, or other fluids, between the proximal portion 152 and the surrounding tissue (e.g., the ascending aorta or the descending aorta). In some cases, proximal portion 152 can provide multiple apertures 158 located adjacent one another. In some cases, proximal portion 152 can include multiple apertures 158 spaced such that the apertures 158 are located in different regions of the heart (e.g., an aperture in the ascending aorta and a second aperture in the descending aorta).

Distal portion 154 can include a curved distal end 156. In some cases, curved distal end 156 can be formed by a deflectable (steerable) portion. Distal portion 154 can include one or more apertures. In some cases, distal portion 154 can be atraumatic.

First catheter assembly 150 can be used to regulate blood flow to provide hemodynamic support. For example, aperture 158 located on proximal portion 152, and an aperture located on the distal portion 154 can be used to control blood flow in and out of the left ventricle 104, and ascending and/or descending aorta 114. In some cases, first catheter assembly 150 can provide bi-directional flow of blood via aperture 158 located on proximal portion 152, and an aperture located on the distal portion 154. In some cases, aperture 158 located on proximal portion 152, and an aperture located on the distal portion 154 can be used to increase stability of first catheter assembly 150 by modulating blood flow in/out of the left ventricle 104 and ascending/descending aorta 114. In some cases, modulating blood flow in/out of the left ventricle 104 and ascending/descending aorta 114 can also aid in the creation of cardiac lesions.

In some cases, motor 162 can provide pumping of fluid (e.g., blood) to regulate blood flow. In some cases, motor 162 can determine a direction of blood flow (e.g., out of left ventricle 104 into aorta 114 or out of aorta 114 into left ventricle 104). In some cases, motor 162 can pump the patient's blood, transfused blood, saline, or other fluids.

In addition, first catheter assembly 150 can include a feedback circuit. Such a feedback circuit can be used to modulate blood flow in/out of the left ventricle 104 and ascending/descending aorta 114. In some cases, the feedback circuit can be coupled to one or more sensors. The sensors can provide information relating to signal ablation, catheter tip impedance, and/or aortic blood pressure waveforms.

Figure 4:
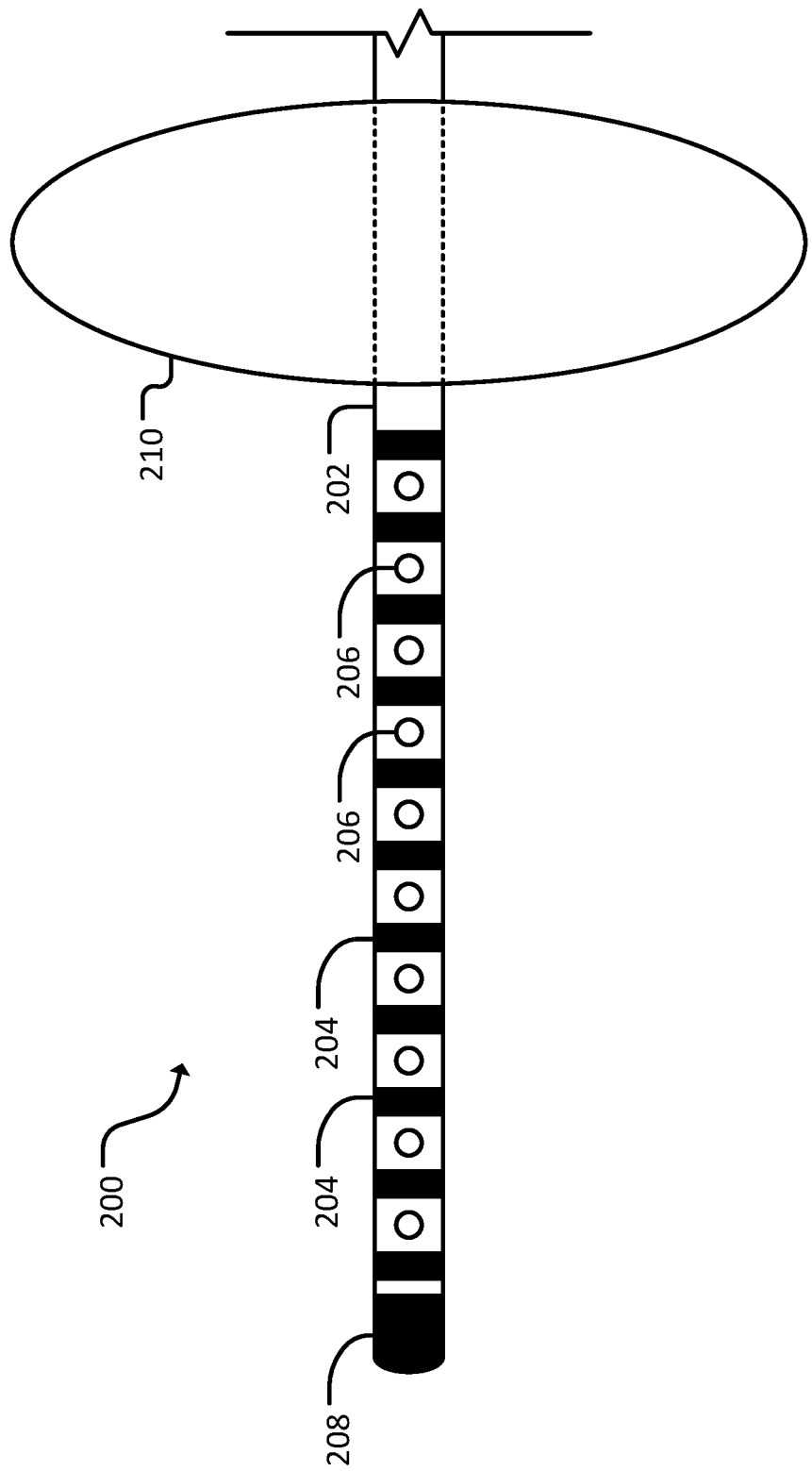
FIG. 4 is a side view of a distal end portion of a second catheter assembly, in accordance with some embodiments provided herein.
Figure 5:
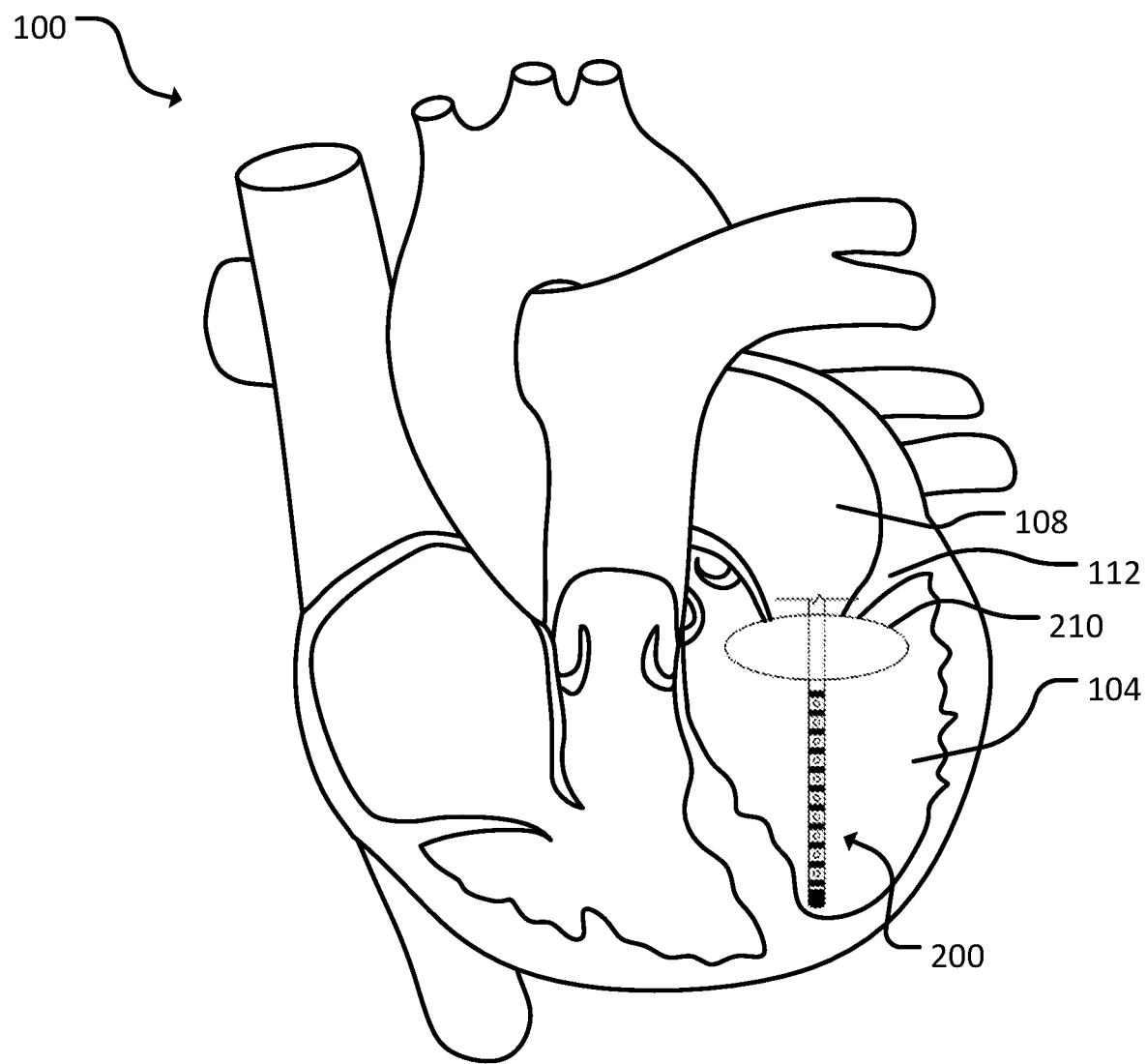
FIG. 5 is a schematic diagram of the second catheter assembly of FIG. 4 in a heart, in accordance with some embodiments provided herein.

Referring to FIGS. 4 and 5, a second catheter assembly 200 can include a catheter 202, a plurality of electrodes 204, a plurality of apertures 206, distal portion 208, and a balloon 210.

Catheter 202 may be a standard catheter. In some cases, catheter 202 is deflectable (steerable). Catheter 202 may be positioned in the right ventricle 102 or the left ventricle 104. Catheter 202 may be inserted via a transapical approach, across the interventricular septum through a transseptal-type puncture, a trans-atrial puncture, or a retrograde aortic approach. In some cases, heart 100 is stopped to insert second catheter assembly 200. In some cases, blood is flushed out of the right ventricle 102 and/or the left ventricle 104 before inserting second catheter assembly 200. In some cases, blood is flushed out of the right ventricle 102 and/or the left ventricle 104 before inflating balloon 210 on second catheter assembly 200. In some cases, heart 100 is stopped during the ablation procedure for a period of time (e.g., 10-12 seconds). In some cases, blood can be aspirated into a distal aperture of catheter 202 in left ventricle 104 and injected into aorta 114 (e.g., ascending aorta and/or descending aorta). In some cases, such an exchange of blood can provide ease for catheter 202 ablation and stability, as well as a method for hemodynamic support for the patient.

Electrodes 204 on catheter 202 can be used to produce an electrical field through a conductive substance inside heart 100. By creating the electrical field, electrodes 204 can perform irreversible electroporation or reversible electroporation. In some cases, electrodes 204 can be uniformly spaced along the distal portion 208 of catheter 202. In some cases, electrodes 204 can be variably spaced along the distal portion of catheter 202. In some cases, electrodes 204 can be monopolar or bipolar. In some cases, a polarity of electrodes 204 can be modified. In some cases, a polarity can be individually selected for each electrode 204. In some cases, electrodes 204 can be selectively disabled. For example, if one electrode 204 is not located in heart 100 when catheter 202 is inserted, that electrode 204 can be disabled. In some cases, electrodes 204 can provide pulses of direct current. In some cases, the electrodes 204 can provide a pulse or a plurality of pulses (e.g., 10 pulses). In some cases, the pulse(s) can have a pulse width (e.g., 90 ms, or 150 ms). In some cases, the pulse(s) can have a delay (e.g., 1-2 seconds between pulses). In some cases, the pulse(s) can be delivered at 750-1500 volts. In some cases, electrodes 204 can be sensing electrodes. In some cases, electrodes 204 can deliver current and sense electrical activity. In some cases, electrodes 204 can provide feedback regarding ablation. In some cases, electrodes 204 can record electrical activity of muscles of heart 100 and/or Purkinje fibers. In some cases, the electrical activity can be displayed in real time and provide feedback. In some cases, the feedback can be used to adjust electroporation parameters (e.g., current parameters and/or solution concentration). In some cases, an electrode 204 can be placed at a distal tip of distal portion 208.

Apertures 206 can be defined by a distal portion of catheter 202. Apertures 206 can be used for aspiration of blood through catheter 202. In some cases, apertures 206 can additionally or alternatively be used to inject a fluid into heart 100. In some cases, apertures 206 can be located on the proximal or distal ends of the catheter tip or the catheter shaft. In some cases, apertures 206 can be in left ventricle 104 and/or aorta 114. In some cases, a volume of fluid injected via apertures 206 can be less than or substantially equal to a volume of blood generally in heart 100, or a portion of heart 100. In some cases, the injected fluid can be a conductive substance (e.g., saline). In some cases, the injected fluid can be the patient's own blood re-circulated during the procedure, transfused blood, or the patient's autologous stored blood. The conductive fluid injected can include, but is not limited to, various saline concentration and non-sodium based salt solutions such as calcium chloride. The conductive fluid injected can be of different viscosity and can include a radio-opaque or fluorescent marker, chemotherapeutic of ablative agent, or a photosensitizer agent delivered locally in small concentrations via the process of electroporation and enhance the ablation ability using light. In some cases, the injected fluid can conduct electric current to deliver irreversible non-contact electroporation and ablation to heart 100. In some cases, the injected fluid can facilitate reversible electroporation by increasing the permeability of cells within heart 100 such that a thereafter injected low dose chemotherapeutic agent that can achieve chemoelectroablation of heart 100. In some cases, apertures 206 can inject alternating cycles of saline and an osmotic reagent in order to deliver phasic DC energy and connect with phasic extracellular material of osmotically active surface altering molecules. In some cases, concentration of the injected fluid can be modified during injection. In some cases, a plurality of apertures 206 can be located on catheter 202. In some cases, a single aperture 206 can be located on catheter 202. In some cases, apertures 206 can be arranged linearly along catheter 202. In some cases, apertures 206 can be arranged circumferentially around catheter 202. In some cases, apertures 206 can be limited to one of aspiration or injection. In some cases, apertures 206 can perform both aspiration and injection. In some cases, apertures 206 can be distributed between electrodes 204.

Balloon 210 can be located on distal portion 208 of catheter 202. In some cases, balloon 210 is proximal electrodes 204 and apertures 206. In some cases, balloon 210 can be compliant to allow second catheter assembly 200 to be maneuvered into place before inflating balloon 210. In some cases, balloon 210 can be inflated in a location such that balloon 210 occludes a valve (e.g., tricuspid valve 110, mitral valve 112, aortic semilunar valve 116, and/or pulmonary semilunar valve). In some cases, when the valve is occluded, the blood can be circulated via the port in the ventricle and pumped to a port in aorta 114. In some cases, balloon 210 can include one or more electrodes on a surface of balloon 210. In some cases, the electrodes on balloon 210 can be sensing and/or delivery electrodes. In some cases, balloon 210 can include one or more apertures on a surface of balloon 210 for aspiration or injection. In some cases, balloon 210 can be inflated with the patient's own blood re-circulated during the procedure, transfused blood, or the patient's autologous stored blood. In some cases, balloon 210 can be disc shaped when inflated. In some cases, balloon 210 can be cylindrical when inflated. In some cases, balloon 210 can be spherical once inflated.

Figure 6:
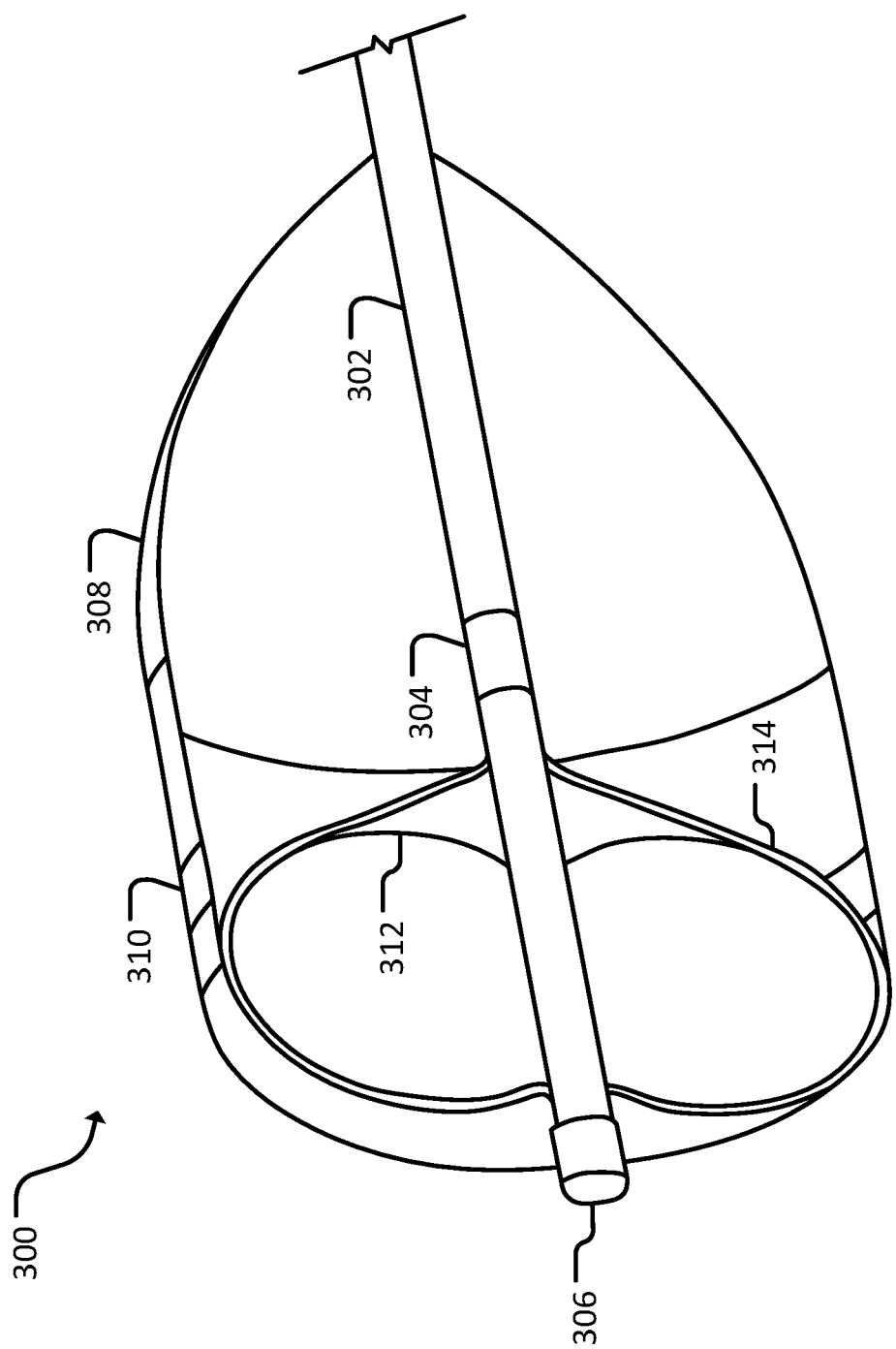
FIG. 6 is a perspective cross-sectional view of a distal end portion of a third catheter assembly, in accordance with some embodiments provided herein.
Figure 7:
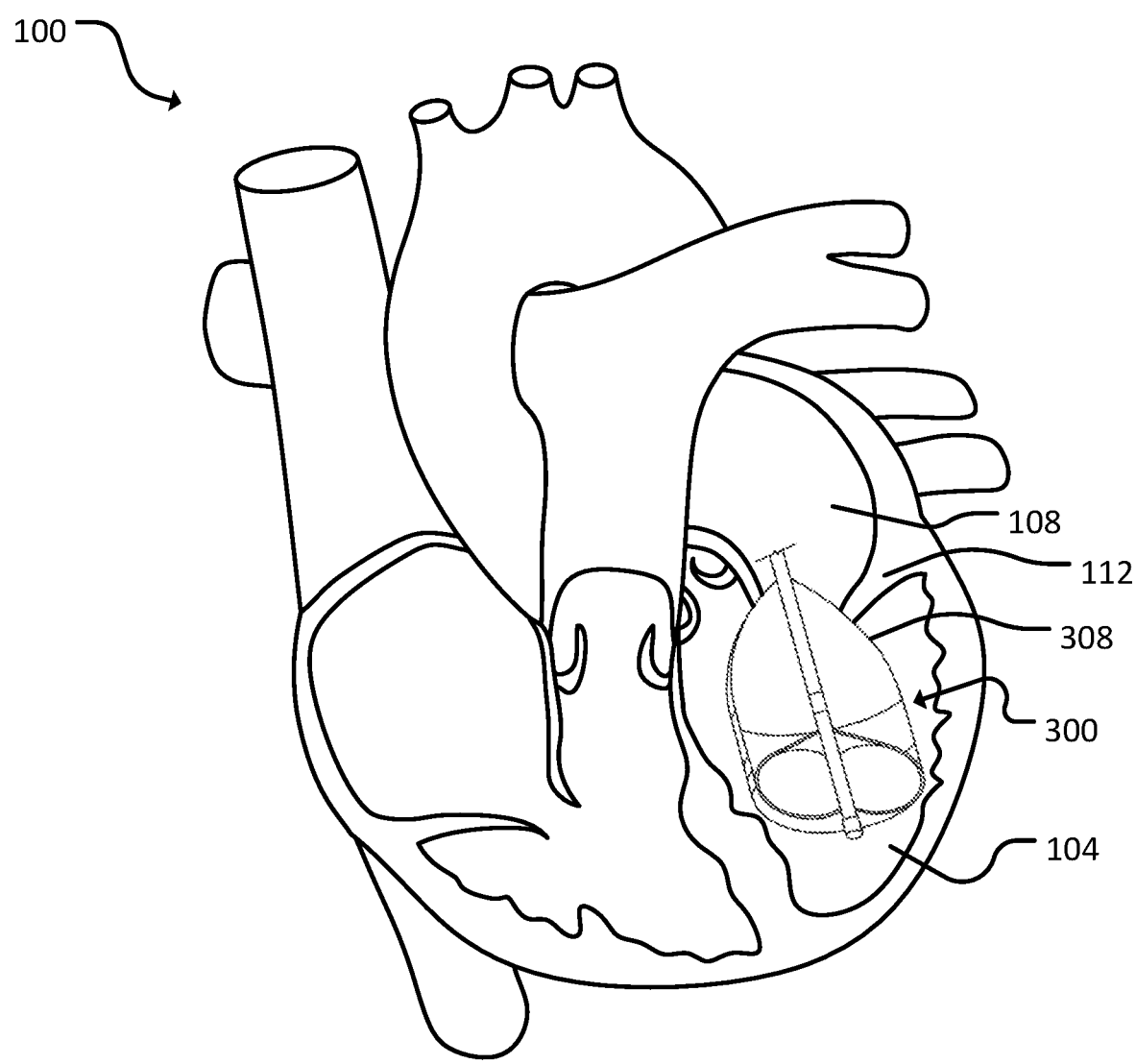
FIG. 7 is a schematic diagram of the third catheter assembly of FIG. 6 in a heart, in accordance with some embodiments provided herein.

Referring to FIGS. 6 and 7, a third catheter assembly 300 can include a catheter 302, an electrode 304, a distal atraumatic tip 306, and a balloon 308. In some cases, balloon 308 can include a porous section 310. In some cases, third catheter assembly 300 can include an inner balloon 312. In some cases, third catheter assembly 300 can include a sensing electrode 314.

Catheter 302 may be a standard catheter. In some cases, catheter 302 is deflectable (steerable). Catheter 302 may be positioned in the right ventricle 102 or the left ventricle 104. Catheter 302 may be inserted via a transapical approach, across the interventricular septum through a transseptal-type puncture, a transatrial puncture or a retrograde aortic approach. In some cases, heart 100 is stopped to insert the third catheter assembly 300. In some cases, blood is flushed out of the right ventricle 102 and/or the left ventricle 104 before inserting third catheter assembly 300. In some cases, blood is flushed out of the right ventricle 102 and/or the left ventricle 104 before inflating balloon 308 on third catheter assembly 300. In some cases, heart 100 is stopped during the ablation procedure for a period of time (e.g., 10-12 seconds). In some cases, fluid can be passed through the patient during the procedure. In some cases, the fluid can be the patient's own blood re-circulated during the procedure, transfused blood, or the patients autologous stored blood through the distal port of the catheter to the proximal port in the aorta 114.

Electrode 304 on catheter 302 can be used to produce an electrical field through a conductive substance inside heart 100. By creating the electrical field, electrode 304 can perform irreversible electroporation or reversible electroporation. In some cases, there can be more than one electrode 304 on catheter 302. In some cases, multiple electrodes 304 can be uniformly spaced along a distal portion of catheter 302. In some cases, multiple electrodes 304 can be variably spaced along the distal portion of catheter 302. In some cases, electrode 304 can be monopolar or bipolar. In some cases, a polarity of electrode 304 can be modified. In some cases, a polarity can be individually selected for each electrode 304 of a plurality of electrodes 304. In some cases, electrode 304 can be selectively disabled. For example, if one electrode 304 is not located in heart 100, or a certain portion of heart 100, when catheter 302 is inserted, electrode 304 can be disabled. In some cases, electrode 304 can provide pulses of direct current. In some cases, the electrode 304 can provide a pulse or a plurality of pulses (e.g., 10 pulses). In some cases, the pulse(s) can have a pulse width (e.g., 90 ms, or 150 ms). In some cases, the pulse(s) can have a delay (e.g., 1-2 seconds between pulses). In some cases, the pulse(s) can be delivered at 750-1500 volts. In some cases, electrode 304 can be a sensing electrode. In some cases, electrode 304 can deliver current and sense electrical activity. In some cases, electrode 304 can provide feedback regarding ablation. In some cases, electrode 304 can record electrical activity of muscles of heart 100 and/or Purkinje fibers. In some cases, the electrical activity can be displayed in real time and provide feedback. In some cases, the feedback can be used to adjust electroporation parameters (e.g., voltage parameters and/or solution concentration). In some cases, electrode 304 can be placed at a distal tip of catheter 302. In some cases, electrode 304 can provide electrical current that can propagate through balloon 308 to deliver the electrical current to heart 100. In some cases, the electrical current can travel through porous section 310 of balloon 208.

Distal atraumatic tip 306 can prevent damage to heart 100 during navigation of third catheter assembly 300. In some cases, distal atraumatic tip 306 can be an electrode, such as electrode 304 described above.

Balloon 308 can be located on a distal portion of catheter 302. In some cases, balloon 310 encompasses electrode 304, such that electrode 304 is inside balloon 308. In some cases, balloon 308 can be compliant to allow third catheter assembly 300 to be maneuvered into place before inflating balloon 308. In some cases, balloon 308 can be inflated in a location such that balloon 308 occludes a valve (e.g., tricuspid valve 110, mitral valve 112, aortic semilunar valve 116, and/or pulmonary semilunar valve). In some cases, balloon 308 abuts a wall of a ventricle (e.g., right ventricle 102 or left ventricle 104) when inflated. In some cases, balloon 308 can inflate to fill a portion (e.g., 25%-75%) of a ventricle (e.g., right ventricle 102 or left ventricle 104). In some cases, balloon 308 can taper as balloon 308 extends proximally. In some cases, once inflated, a portion of balloon 308 can remain in a valve (e.g., tricuspid valve 110, mitral valve 112, aortic semilunar valve 116, and/or pulmonary semilunar valve). In some cases, approximately two-thirds of balloon 308 can be within a ventricle (e.g., right ventricle 102 or left ventricle 104), while one-third of balloon 308 remains in a valve and/or an atrium (e.g., right atrium 106 or left atrium 108). In some cases, balloon 308 can push against a valve (e.g., tricuspid valve 110, mitral valve 112, aortic semilunar valve 116, and/or pulmonary semilunar valve) from a ventricular side to occlude the valve. In some cases, balloon 308 can include one or more electrodes on a surface of balloon 308. In some cases, the electrodes on balloon 308 can be sensing and/or delivery electrodes. In some cases, balloon 308 can include one or more apertures on a surface of balloon 308.

Porous section 310 of balloon 308 can be a porous material. In some cases, porous section 310 can be a designated section of balloon 308. In some cases, balloon 308 can include multiple porous sections 310. In some cases, porous section 310 can surround a circumference of balloon 308.

Inner balloon 312 can be inflated inside balloon 308. Inner balloon 312 can be located at a distal portion of catheter 302. In some cases, inner balloon 312 can be inflated separately from balloon 308. In some cases, inner balloon 312 can include a recording or sensing electrode 314.

Sensing electrode 314 can be located on inner balloon 312. In some cases, sensing electrode 314 can be coupled to inner balloon 312. In some cases, sensing electrode 314 can move with balloon 312, such that sensing electrode 314 expands and/or contracts with inner balloon 312. In some cases, sensing electrode 314 can provide assistance with navigation. In some cases, sensing electrode 314 can record Purkinje signals. In some cases, the Purkinje signals can be fed into a feedback system. The feedback system can modify energy delivery and/or a concentration of injected fluid. In some cases, the feedback system can modulate flow of blood and/or saline to modulate catheter stability. In some cases, the feedback loop can provide hemodynamic support during refractory ventricular tachycardia/ventricular fibrillation. In some cases, the feedback system can cease energy delivery. In some cases, the feedback system monitors a characteristic electrogram of the Purkinje signals with automated monitoring of the signals based on real-time changes such as diminution or fragmentation. In some cases, once electrogram of Purkinje signals is eliminated, energy delivery can be automatically shut off. In some cases, sensing electrode 314 can provide electroporation energy to heart 100. In some cases, sensing electrode 314 can provide energy to pace the ventricular myocardium. In some cases, loss of capture and/or pacing can render an indication that ablation is complete and successful.

Figure 8:
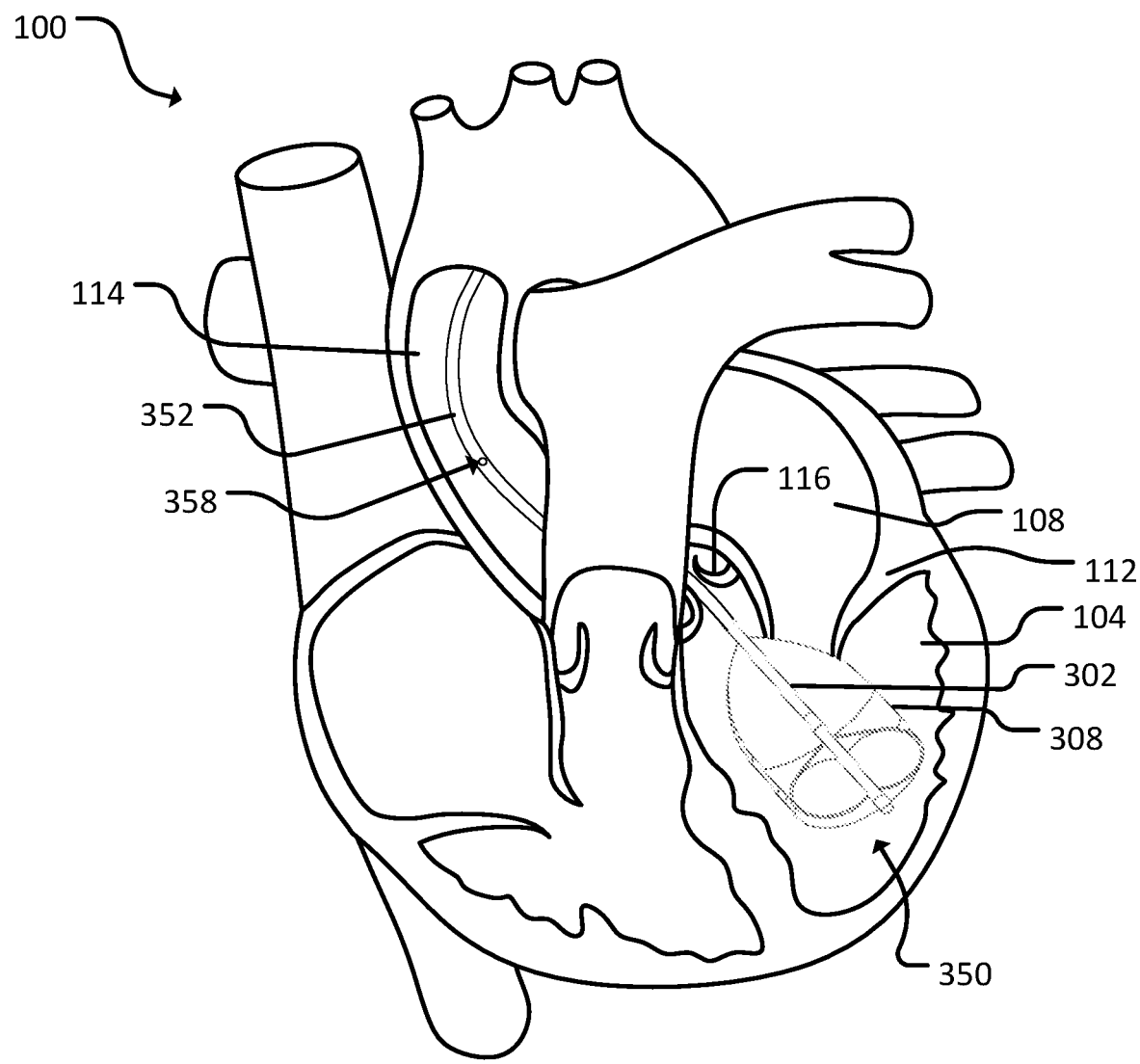
FIG. 8 is a schematic diagram of a fourth catheter assembly in a heart, in accordance with some embodiments provided herein.

Referring to FIG. 8, a fourth catheter assembly 350 be substantially similar to third catheter assembly 300. In some cases, catheter assembly 350 can be implanted substantially similar to third catheter assembly 300. Fourth catheter assembly 350 can include catheter 302 with a proximal portion 352. Balloon 308 can be located at a distal portion of catheter 302. Proximal portion 352 can reside in the ascending or descending aorta 114, while balloon 308 resides in the left ventricle 104.

Proximal portion 352 can include an aperture 358 that can provide inflow and outflow of blood, or other fluids, between the proximal portion 352 and the surrounding tissue (e.g., the ascending aorta or the descending aorta). In some cases, proximal portion 352 can provide multiple apertures 358 located adjacent one another. In some cases, proximal portion 352 can include multiple apertures 358 spaced such that the apertures 358 are located in different regions of the heart (e.g., an aperture in the ascending aorta and a second aperture in the descending aorta).

As described with respect to FIGS. 6 and 7, balloon 308 can be located on a distal portion of fourth catheter assembly 350. In some cases, balloon 308 can include one or more apertures on a surface of balloon 308. In some cases, balloon 308 can include a porous section that is made of a porous material such that fluid can between an interior and an exterior of balloon 308. In some cases, an aperture can be located on a portion of catheter 302 that is distal to balloon 308.

Fourth catheter assembly 350 can be used to regulate blood flow to provide hemodynamic support in addition to providing ablation. For example, aperture 358 located on proximal portion 352, and an aperture located on the distal portion of catheter 302 (e.g., on balloon 308 or distal balloon 308) can be used to control blood flow in and out of the left ventricle 104, and ascending/descending aorta 114. In some cases, fourth catheter assembly 350 can provide bi-directional flow of blood via aperture 358 located on proximal portion 352, and an aperture located on the distal portion of catheter 302. In some cases, aperture 358 located on proximal portion 352, and an aperture located on the distal portion of catheter 302 can be used to increase stability of fourth catheter assembly 350 by modulating blood flow in/out of the left ventricle 104 and ascending/descending aorta 114. In some cases, modulating blood flow in/out of the left ventricle 104 and ascending/descending aorta 114 can aid in the creation of cardiac lesions.

In some cases, fourth catheter assembly 350 can be coupled to a motor (e.g., a pump). In some cases, the motor can provide pumping of fluid (e.g., blood) to regulate blood flow. In some cases, the motor can determine a direction of blood flow (e.g., out of left ventricle 104 into aorta 114 or out of aorta 114 into left ventricle 104). In some cases, the motor can pump the patient's blood, transfused blood, saline, or other fluids.

In some cases, fourth catheter assembly 150 can include a feedback circuit. Such a feedback circuit can be used to modulate blood flow in/out of the left ventricle 104 and ascending/descending aorta 114. In some cases, the feedback circuit can be coupled to one or more sensors. The sensors can provide information relating to signal ablation, catheter tip impedance, and/or aortic blood pressure waveforms.

Figure 9:
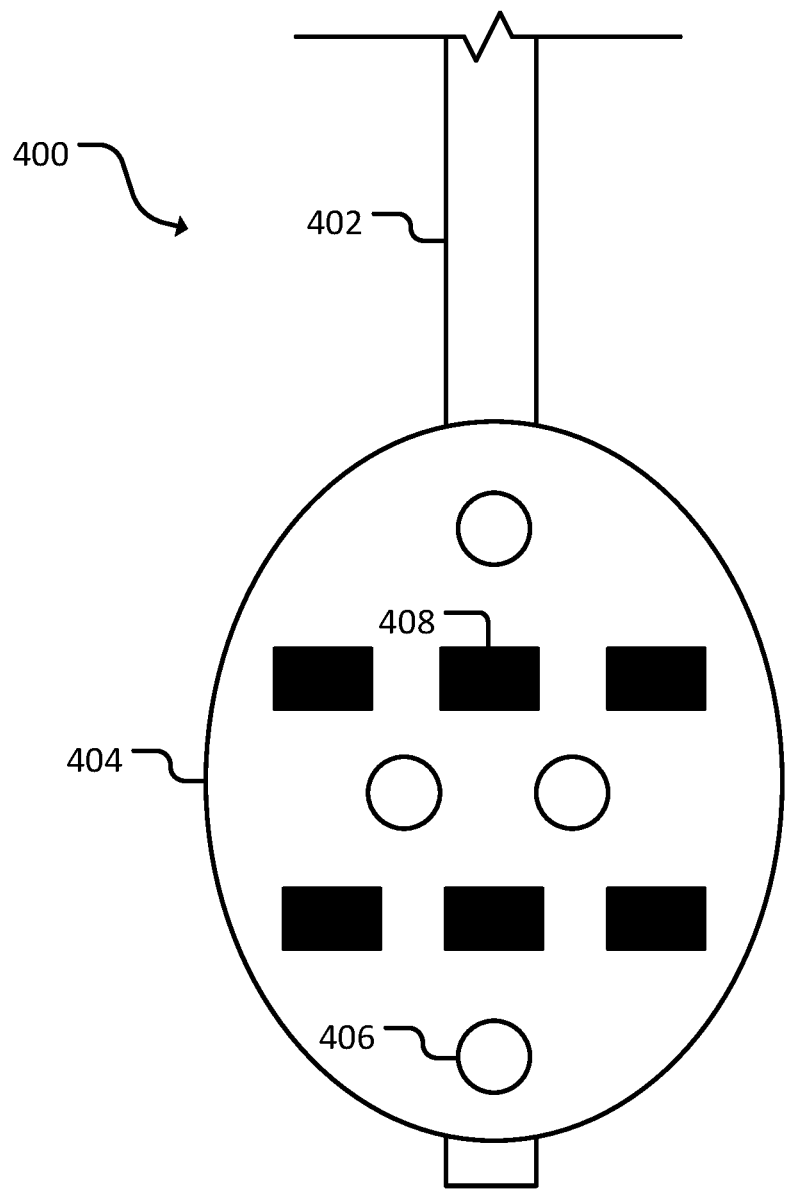
FIG. 9 is a perspective view of a distal end portion of a fifth catheter assembly, in accordance with some embodiments provided herein.
Figure 10:
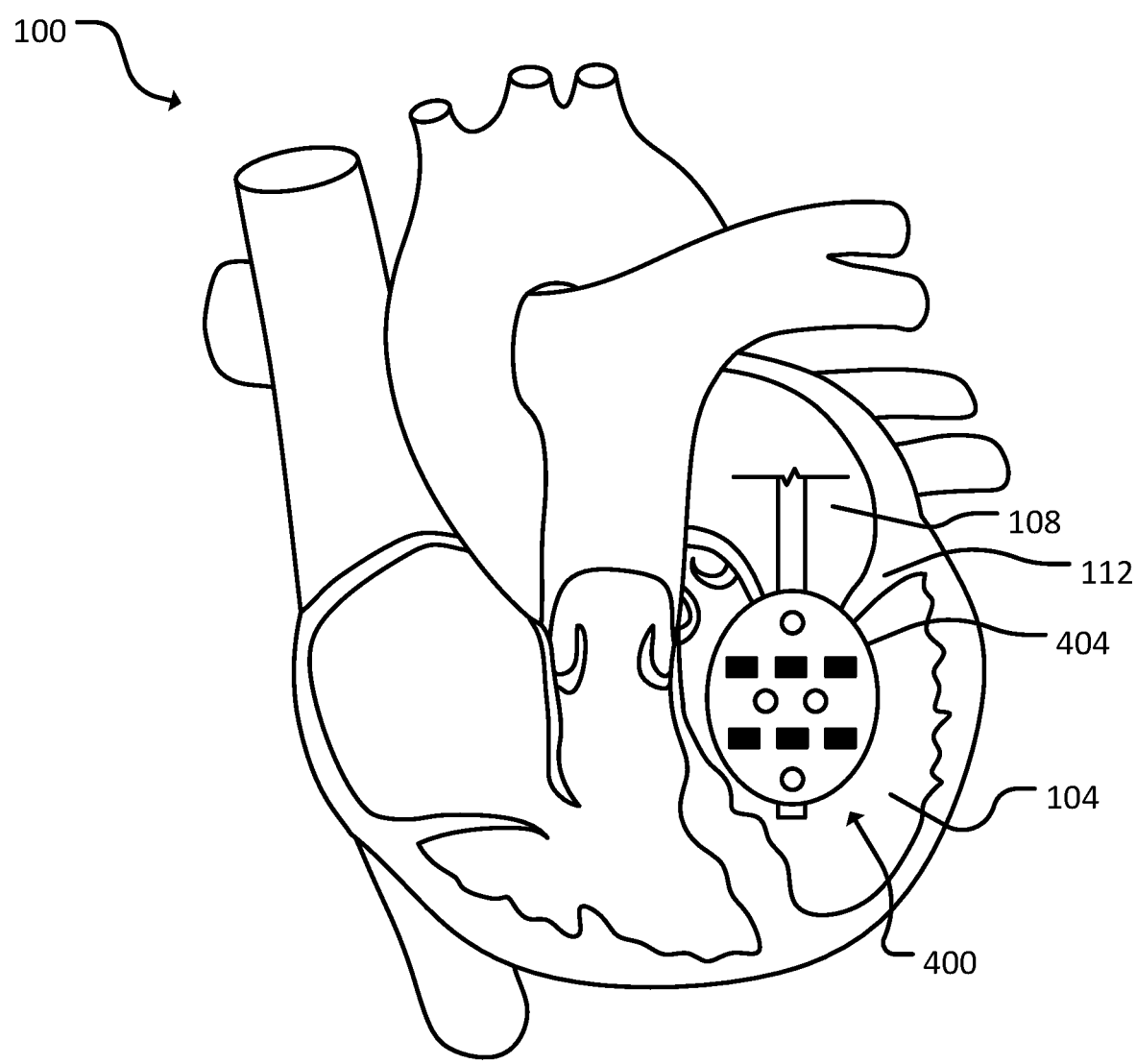
FIG. 10 is a schematic diagram of the fifth catheter assembly of FIG. 9 in a heart, in accordance with some embodiments provided herein.

Referring to FIGS. 9 and 10, a fifth catheter assembly 400 can include a catheter 402 and a balloon 404. In some cases, balloon 404 can include one or more apertures 406. In some cases, balloon 404 can include one or more electrodes 408.

Catheter 402 may be a standard catheter. In some cases, catheter 402 is deflectable (steerable). Catheter 402 may be positioned in the right ventricle 102 or the left ventricle 104. Catheter 402 may be inserted via a transapical approach, across the interventricular septum through a transseptal-type puncture, a transatrial puncture or a retrograde aortic approach. In some cases, heart 100 is stopped to insert fifth catheter assembly 400. In some cases, blood is flushed out of the right ventricle 102 and/or the left ventricle 104 before inserting fifth catheter assembly 400. In some cases, blood is flushed out of the right ventricle 102 and/or the left ventricle 104 before inflating balloon 404 on fifth catheter assembly 400. In some cases, heart 100 is stopped during the ablation procedure for a period of time (e.g., 10-12 seconds). In some cases, the hemodynamic support provided by the catheter ports in the ventricle and aorta 114 with an outside circuit can produce sustainable blood pressure to continue mapping and ablation and prevent hemodynamic deterioration during incessant ventricular tachycardia/ventricular fibrillation.

Balloon 404 can be located on a distal portion of catheter 402. In some cases, balloon 404 can be compliant to allow fifth catheter assembly 400 to be maneuvered into place before inflating balloon 404. In some cases, balloon 404 can be inflated in a location such that balloon 404 occludes a valve (e.g., tricuspid valve 110, mitral valve 112, aortic semilunar valve 116, and/or pulmonary semilunar valve). In some cases, balloon 404 abuts a wall of a ventricle (e.g., right ventricle 102 or left ventricle 104) when inflated. In some cases, balloon 404 can inflate to fill a portion (e.g., 25%-75%) of a ventricle (e.g., right ventricle 102 or left ventricle 104). In some cases, balloon 404 can taper as balloon 404 extends proximally. In some cases, once inflated, a portion of balloon 404 can remain in a valve (e.g., tricuspid valve 110, mitral valve 112, aortic semilunar valve 116, and/or pulmonary semilunar valve). In some cases, approximately two-thirds of balloon 404 can be within a ventricle (e.g., right ventricle 102 or left ventricle 104), while one-third of balloon 404 remains in a valve and/or an atrium (e.g., right atrium 106 or left atrium 108). In some cases, balloon 404 can push against a valve (e.g., tricuspid valve 110, mitral valve 112, aortic semilunar valve 116, and/or pulmonary semilunar valve) from a ventricular side to occlude the valve. In some cases, balloon 404 can include one or more electrodes 408 on a surface of balloon 308. In some cases, the electrodes 408 on balloon 308 can be sensing and/or delivery electrodes. In some cases, balloon 308 can include one or more apertures 406 on a surface of balloon 404.

Apertures 406 can be used for aspiration of blood through catheter 402. In some cases, apertures 406 can additionally or alternatively be used to inject a fluid into heart 100. In some cases, a volume of fluid injected via apertures 406 can be less than or substantially equal to a volume of blood generally in heart 100, or a portion of heart 100. In some cases, the injected fluid can be a conductive substance (e.g., saline). The conductive fluid injected can include, but is not limited to, various saline concentration and non-sodium based salt solutions such has calcium chloride. The conductive fluid injected can be of different viscosity and can include a radio-opaque or fluorescent marker, chemotherapeutic of ablative agent, or a photosensitizer agent delivered locally in small concentrations via the process of electroporation and enhance the ablation ability using light. In some cases, the injected fluid can conduct electric current to deliver irreversible non-contact electroporation and ablation to heart 100. In some cases, the injected fluid can facilitate reversible electroporation by increasing the permeability of cells within heart 100 such that a thereafter injected low dose chemotherapeutic agent that can achieve chemoelectroablation of heart 100. In some cases, apertures 406 can inject alternating cycles of saline and an osmotic reagent in order to deliver phasic DC energy and connect with phasic extracellular material of osmotically active surface altering molecules. In some cases, concentration of the injected fluid can be modified during injection. In some cases, a plurality of apertures 406 can be located on balloon 404. In some cases, a single aperture 406 can be located on balloon 404. In some cases, apertures 406 can be arranged linearly along balloon 404. In some cases, apertures 406 can be arranged circumferentially around balloon 404. In some cases, apertures 406 can be limited to one of aspiration or injection. In some cases, apertures 406 can perform both aspiration and injection. In some cases, apertures 406 can be distributed between electrodes 408.

Electrode 408 balloon 404 can be used to produce an electrical field through a conductive substance inside heart 100. By creating the electrical field, electrode 408 can perform irreversible electroporation or reversible electroporation. In some cases, there can be more than one electrode 408 on balloon 404. In some cases, multiple electrodes 408 can be uniformly spaced along a distal portion of balloon 404. In some cases, multiple electrodes 408 can be variably spaced around balloon 404. In some cases, electrode 408 can be monopolar or bipolar. In some cases, a polarity of electrode 408 can be modified. In some cases, a polarity can be individually selected for each electrode 408 of a plurality of electrodes 408. In some cases, electrode 408 can be selectively disabled. For example, if one electrode 408 is not located in heart 100, or a certain portion of heart 100, when catheter 402 is inserted, electrode 408 can be disabled. In some cases, electrode 408 can provide pulses of direct current. In some cases, the electrode 408 can provide a pulse or a plurality of pulses (e.g., 10 pulses). In some cases, the pulse(s) can have a pulse width (e.g., 90 ms, or 150 ms). In some cases, the pulse(s) can have a delay (e.g., 1-2 seconds between pulses). In some cases, the pulse(s) can be delivered at 750-1500 volts. In some cases, electrode 408 can provide assistance with navigation. In some cases, electrode 408 can be a sensing electrode. In some cases, electrode 408 can deliver current and sense electrical activity. In some cases, electrode 408 can provide feedback regarding ablation. In some cases, electrode 408 can record electrical activity of muscles of heart 100 and/or Purkinje fibers. In some cases, the electrical activity can be displayed in real time and provide feedback. In some cases, the feedback can be used to adjust electroporation parameters (e.g., current parameters and/or solution concentration). In some cases, the feedback system can cease energy delivery. In some cases, the feedback system monitors a characteristic electrogram of the Purkinje signals with automated monitoring of the signals based on real-time changes such as diminution or fragmentation. In some cases, once electrogram of Purkinje signals is eliminated, energy delivery can be automatically shut off. In some cases, electrode 408 can provide energy to pace the ventricular myocardium. In some cases, loss of capture and/or pacing can render an indication that ablation is complete and successful.

While modulation of blood flow is described with respect to FIGS. 2, 3, and 8, such a catheter configuration and implementation can be implemented into any of the embodiments described herein.

In some cases, a drug for cellular modulation of Purkinje tissue can be delivered using the catheters and methods described herein. Such an implementation of delivering a drug locally via catheter based electroporation can provide enhanced delivery, efficiency, and safety for human clinical use. In some cases, the drug can be a combination of a peptide toxin, or other cardio-neural toxins found in nature. Such a peptide toxin can alter the flux of ions across the cellular lipid bilayer. In some cases, the peptide toxin can include Anthopleurin-A toxin, Heteropoda 2 toxin, and/or Sea Nettle toxin. These toxins can have an affinity for altering the transmembrane potential of Purkinje cells and thus can be used as an anti-arrhythmic agent. A benefit to peptide toxins is these drugs can be highly specific with regards to the mechanism of action. For example, unlike some drugs which can affect multiple ion channels because their mechanism is blocking the pore of ion channels, the peptide toxin can target a specific aspect of a specific ion channel. For example, Heteropoda 2 toxin can be specific for Kv4 potassium ion channels, and can module channel gating kinetics at an S3-S4 extracellular linker domain, away from the pore, which have an affinity for Purkinje cells over myocardial cells. Similarly, Anthopleurin-A toxin can bind to an SIII extracellular linker region in sodium ion channels, away from the sodium channel pore. In addition, Sea Nettle toxin can exert membrane active changes by creating lipid membrane pores, which can create ion flux across the membrane. In some cases, the drug and/or toxin can affect the gating of ion channels of Purkinje cells in other domains. For example, alteration to the lipid bilayer which can activate stretch channels, which can cause ion channel flux. In some cases, drugs can be administered that have an effect intracellularly on either membrane proteins and/or inner leaflets of the membrane bilayer, and/or alter proteins important in affecting ion channel permeation, known as ancillary subunits. For example, the channel anciallary subunits can include KChip, KChap, Beta subunits, etc., which favor different modulation channels to aid in stopping an arrhythmia. For example, the ancillary subunits can have mechanisms directed to enhancing and/or favoring the closed, inactive, or open states of ion channels, which can disrupt electrical circuits for arrhythmias. In some cases, drugs for both extracellular and intracellular activation and modulation can be delivered. In some cases, drugs that effect intracellular signaling cascades from the extracellular surface, within the lipid bilayer or intracellular surface, can be used to activate signaling cascades, such as PIP2, PKC, PKA, etc.

In some cases, using the catheters provided herein, the various drugs can be delivered locally. For example, the drug can be delivered to the Purkinje conduction tissue in the ventricle, where a focus of pro-arrhythmic activity can be disrupted. In some cases, the drug can be administered in addition to delivering electroporation to the ventricle. The electroporation can alter the cellular lipid bilayer by providing an electrical or magnetic field to the tissue site of interested, while the drug is being administered locally. In some cases, a pulsed DC electroporation current can be used. In some cases, the drug can be administered simultaneously with the delivery of electroporation. Such a combination of electroporation and drug delivery can promote the update of the drug into the cell, and thus add to the safety and specificity profile of the drug. For example, electroporation can open the cell membrane, the drug can be administered and taken into the cell, and then electroporation can be used to seal the cell membrane. In some cases, the drug can be administered in isotonic saline with albumin (e.g., 5% albumin), to allow protein-drug binding and provide a lipophilic partitioning to favor membrane portioning to alter bilayer proteins to create changes in transmembrane potential.

In some cases, to target delivery of drugs to specific tissue (e.g., Purkinje tissue), in addition to administering the drug locally, the electroporation can be modified to facilitate uptake of the drug by the specific tissue. For example, parameters (e.g., duration, timing, number, and/or amplitude) of electroporation can be modulated. In some cases, parameters of electroporation can be selected such that reversible electroporation is delivered. In some cases, reversible electroporation for Purkinje cells can allow the cells to "open" and "close," and thus capturing the drug inside the cells. In some cases, inversions of pulse polarity of electroporation can be used to leverage the specificity of drug delivery and retention in tissues of interest. In some cases, parameters of electroporation can be used to preferentially open membranes for enhanced selectivity of tissue (e.g., Purkinje uptake and not ventricular myocardial uptake).

In some cases, electroporation could be used solely as a means to increase uptake of drugs into cells, which can increase safety and selectivity of the procedure. In some cases, the electroporation can allow for uptake and retention in the cells and molecular ablation can take place. In some cases, reversible electroporation can be used to re-seal the cell. In some cases, irreversible electroporation can be delivered after reversible electroporation.

In some embodiments, a distal portion (e.g., a tip) of the catheter can include a sensor. In some cases, the sensor can detect an extracellular concentration of sodium, potassium, calcium, pH, etc. In some cases, the sensor can be in communication with a feedback circuit, such that electroporation is ceased when once the cellular expulsion into the local extracellular milieu is complete.

In some cases, irreversible electroporation can be delivered without the delivery of reversible electroporation. In some cases, the combination of electroporation and drug administration can reduce the concentration and/or amount of drug necessary to facilitate the same effects without electroporation. Such a decrease in amount and/or concentration of the drug administered can enhance the safety profile of the procedure. In some cases, the combination of electroporation and drug administration can reduce the energy required for electroporation. For example, drugs can be administered to specific tissues prior to electroporation. In some cases, the drug uptake can lower the threshold for cells to be ablated. Such a lowered threshold can enhance the safety and efficacy of ablation. In some cases, by lowering the threshold for electroporation, and/or ablation, the specific tissues can be more readily targeted, as the energy for electroporation would be sub-threshold when compared to surrounding tissue due to the differential of drug uptake.

In some cases, various methods can be used to increase time and/or surface area contact to allow for maximum cellular uptake of the drug. In some cases, such methods can alleviate or reduce the concern for drug washout through the systemic circulation from a beating heart. In some cases, a drug can be used to slow and/or stop the heart to allow for more time for drug activity. In some cases, the catheter assembly can include an adaptable catheter tip to enhance tissue-catheter contact. For example, the catheter tip can create a vacuum seal between the tissue and the catheter tip to allow for selective drug delivery and prevention of drug washout in the circulation. In some cases, the catheter tip can be deflectable to aid in positioning the catheter tip in proximity with the tissue.

In some cases, the systems and methods provided herein can provide reversible and transient termination of conduction in response to specific times when an arrhythmia takes place. Such a configuration can be an alternative form of defibrillation. For example, a drug delivery system can be attached to, or in communication with, the heart and can release a Purkinje specific drug and a low level current (e.g., DC current) to permit Purkinje specific penetration of the therapeutic agent. In some cases, systemic effects can be reduced using a combination of electroporation and drug delivery. In some cases, the Purkinje specific drug can be reversible in the effect caused by the drug, but allow for acute termination of the arrhythmia. In some cases, the system can include a mesh like portion with penetrating ports that are applied epicardially to the heart or a network applied along the endocardial surface with the capacity to deliver either a fluid or semi-fluid agent as well as a DC electric current.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the process depicted in the accompanying figures do not necessarily require the particular order shown, or sequential order, to achieve desirable results. In certain implementations, multitasking and parallel processing may be advantageous.

What is claimed is:

1. A method of performing electroporation of a ventricle, the method comprising:
    inserting a distal end portion of a catheter into the ventricle of a heart of a patient, the distal end portion of the catheter comprising:
        a catheter shaft
        a balloon coupled to the catheter shaft;
        a plurality of electrodes coupled to a distal-most portion of the catheter shaft that extends distally of the balloon,
        wherein the distal-most portion of the catheter shaft defines a plurality of apertures, each aperture of the plurality of apertures positioned between two adjacent electrodes of the plurality of electrodes;
    inflating the balloon coupled to the catheter shaft;
    using the balloon to push against and occlude a mitral valve or a tricuspid valve of the heart;
    while the mitral valve or the tricuspid valve is being occluded by the balloon, injecting a fluid from a lumen of the distal end portion of the catheter, through the plurality of apertures defined by the distal-most portion of the catheter shaft, and directly into the ventricle; and
    while the mitral valve or the tricuspid valve is being occluded by the balloon, generating an electrical current via at least one electrode of the plurality of electrodes so as to selectively deliver electroporation to Purkinje tissue in the ventricle using the fluid in the ventricle as an electrical conductor,
    wherein selectively delivering the electroporation to the Purkinje tissue in the ventricle causes minimal damage to a healthy heart tissue in the ventricle.

2. The method of claim 1, wherein the balloon comprises a porous section to allow the fluid to pass through the balloon.

3. The method of claim 1, further comprising: (i) removing blood from the ventricle; and (ii) wherein injecting the fluid further comprises injecting alternating cycles of saline and an osmotic reagent.

4. The method of claim 1, further comprising sensing signals from the Purkinje tissue.

5. The method of claim 4, further comprising modifying a parameter of the electrical current or a concentration of the fluid based on the signals.

6. The method of claim 1, further comprising modulating a flow of blood into and out of the ventricle via at least one aperture of the plurality of apertures, wherein the flow of blood is modulated via a proximal aperture on a proximal portion of the catheter, and wherein the proximal portion of the catheter is positioned in an aorta.

7. The method of claim 6, further comprising modulating the flow of blood into and out of the aorta.

8. The method of claim 6, wherein modulating the flow of blood comprises pumping blood via a pump located outside the patient.

9. The method of claim 6, wherein modulating the flow of blood comprises the injection of the fluid to the ventricle, wherein the fluid is at least one of blood of the patient, a transfused blood, or saline.

10. The method of claim 1, further comprising monitoring a parameter, wherein the parameter is at least one of an ablation signal, an impedance of the distal end portion of the catheter, or an aortic blood pressure waveform.

* * * * *